(12) United States Patent
De Montalembert

(10) Patent No.: US 6,494,662 B1
(45) Date of Patent: Dec. 17, 2002

(54) DEVICE FOR REMOTE CONTROL OF THE MOVEMENT OF GRIPPING ELEMENTS

(75) Inventor: Charles De Montalembert, Paris (FR)

(73) Assignee: Compagnie Generale de Participations, Luxembourg (LU)

( * ) Notice: Subject to any disclaimer, the term of this patent is extended or adjusted under 35 U.S.C. 154(b) by 0 days.

(21) Appl. No.: 09/719,558

(22) PCT Filed: Apr. 26, 2000

(86) PCT No.: PCT/FR00/01113

§ 371 (c)(1),
(2), (4) Date: Feb. 27, 2001

(87) PCT Pub. No.: WO00/64386

PCT Pub. Date: Nov. 2, 2000

(30) Foreign Application Priority Data

Apr. 27, 1999 (FR) ............................................. 99 05318

(51) Int. Cl.[7] .................................................. B25J 3/00
(52) U.S. Cl. ........................ 414/1; 192/93 A; 192/223.3
(58) Field of Search ........................... 414/1, 7; 901/36; 192/223.3, 54.5, 93 A; 294/106, 111; 623/57, 58, 63

(56) References Cited

U.S. PATENT DOCUMENTS 2,493,776 A    1/1950   Pecorella et al.

FOREIGN PATENT DOCUMENTS

FR    2 236 478    6/1976
FR    2 557 450    5/1986
FR    2 665 833    2/1992

Primary Examiner—Donald W. Underwood
(74) Attorney, Agent, or Firm—Jacobson Holman PLLC

(57) ABSTRACT

Remote control of a mechanical transmission, more particularly to the remote control of at least one gripping element by a monodirectional action, whereby the gripping element includes an articulation which can close by converging upon the object which is to be gripped and which can be locked in an active position upon contact with said object and the control device can be disengaged in the gripping position. The device includes a) a primary pulley which is joined to a control cable; b) a spring which angularly returns the primary pulley to its initial position counter to the action of the cable; c) a secondary pulley which is joined to the end of the output cable terminating in the elements which are to be controlled; d) a self-disengaging mechanical drive disc which, for a torque value exceeding a given threshold, can displace the secondary pulley in a disengaged position; e) a locking ring for the second pulley in a disengaged position; f) opposing trapezoid-shaped teeth on opposite surfaces of the disk and secondary pulley, whereby the pulley can be alternatively driven by ring dogging by the disk and the teeth can be disengaged by a cam effect on the basis of a given torque.

15 Claims, 6 Drawing Sheets

DEVICE FOR REMOTE CONTROL OF THE MOVEMENT OF GRIPPING ELEMENTS

The present invention relates to the field of devices for remote control of movement. More particularly, the invention concerns a single device for remote control of elements, particularly gripping elements, such as articulated jaws or fingers and adapted to converge upon the object to be gripped.

The invention is particularly applicable to the control of an element having to be placed successively in active position, position in which the element is blocked, then disengaged from this blocked active position, the control of the cycle being permitted from one sole movement transmission means, with unidirectional linear or angular action. The same manoeuvre of the transmission means makes it possible, when the controlled element is inactive, to take it towards its blocked active position, and when the controlled element is in blocked active position, a fresh manoeuvre identical to the preceding one returns it towards its inactive starting position.

The invention is particularly applicable to the control of elements for gripping and displacing objects, forming an artificial hand usable for the remote manipulation of objects in an aggressive or dangerous environment; the invention will also be more particularly applicable to the production of a manual prosthesis controlled by cable, for example from a scapular or dorsal harness and transmitting to the articulated fingers an effort of traction taking the fingers towards their gripping position. It is in connection with this latter application that the invention will be described hereinafter, although it does not constitute the limiting framework of application of the device described and claimed here. The latter may in effect be adapted to the control of numerous bistable systems moving between two positions of rest, the same unidirectional manoeuvre of a single transmission means operating the passage from one position to the other.

Numerous systems of manual prostheses are known, aiming at allowing persons having undergone an amputation of the hand, to perform certain gestures or certain elementary functions of everyday life, both personal and social, and in particular and especially the bi- or pluridigital gripping of objects, under conditions reproducing more or less faithfully the gripping functions of the natural hand.

French Patents Nos. 73 25719, 83 15850 and 90 10455 for example disclose a hand prosthesis constituted by a rigid plate forming palm supporting articulated elements forming the phalanxes, the latter being provided with an inner spring made of elastically deformable material and returning the corresponding finger in position of extension, a terminal cable connected to the end of each finger being adapted to provoke the movement of angular closure of the finger; the terminal cables are connected to a common beam or bar distributing the traction transferred successivly on each of the terminal cables, this traction coming from a single cable controlled by the user, for example from a dorsal harness. This mechanical structure is completed by a surfacing or trim both for facing and functional, viz. a rigid or semi-rigid dorsal shell and a coating made of supple material, particularly cellular on the palm face.

The invention relates to a device for transmitting and controlling the effort of traction operating from the single cable and driving terminal cables for individual control of the fingers belonging to a manual prosthesis, in particular of the type such as provided by the above-mentioned Patents; reference is expressly made to these Patents for a more complete description of the elements ensuring the functionality and the aesthetically satisfactory aspect of the prosthesis.

According to Patents 83 15850 and 90 10455, a device has been provided for locking the traction arriving at the beam for balancing and distribution on the terminal cables. The object of the devices provided in these Patents is to make it possible to block the gripping elements, particularly the fingers once closed on the object gripped; such blocking allows comfort of use in that it allows a relaxing of the effort of traction having controlled the retraction of the fingers and the grip of the object. Thus the user may, without maintaining his/her effort, conserve in manually held position the gripped object which is in that case capable of being displaced or changed in its positioning in space. In effect, it will be understood that it is particularly hard and difficult for the user to ensure at the same time the maintaining of a traction ensuring stability of the grip and, in parallel, a manipulation or a manoeuvre of the object held in the hand.

The mechanical blocking devices according to the aforementioned Patents employ elements acting on the traction cable, either directly by pinching or braking, or via means associated with the cable and subjected to a locking catch. In this way an immobilization of the cable in the position of the closed fingers in abutment on the object is obtained, despite the stop of any traction voluntarily controlled by the user on the cable. Despite their interest and efficiency, these known devices remain imperfect. In effect, although their actuation towards the blocking position can be controlled automatically, for example by a return spring controlling the displacement towards its active position of the locking catch constituted by a pawl associated with a rack or a ratchet wheel, unblocking of the locking system requires a specific manoeuvre and an intervention of the other hand, which handicaps and slows down the overall operation of the ongoing manipulation.

A first object of the invention is to provide a system for locking the hand in position where the fingers are closed on the gripped object, which locking automatically occurs at the end of the phase of closure, the fingers having arrived in position of abutment on the gripped object; this system allows a relaxing of the voluntary effort of traction, while ensuring maintenance of the gripping position acquired.

A second object of the invention is to allow an unlocking which occurs when the user desires, therefore at the opportune moment, solely by manoeuvring the traction cable, while allowing the user to resume, at the moment of release of the fingers, the control of the gripping position previously set. More especially according to this object of the invention, after a period of rest of the traction cable, the maintained grip no longer being under the voluntary control of the user, the latter can in one and the same manoeuvre return to the gripping position voluntarily controlled by the traction cable via an autonomous action of unlocking of the gripping elements, by means of a single subsequent action on the single cable.

Another object of the invention is to introduce in the functioning of the artificial hand a comfort and convenience of control such as a precision of the gesture, by an effect of demultiplication of the movement between the movement of control and the displacement of the remote-controlled elements.

Finally, an essential object of the invention is to allow the use of a single movement control means, for example a linear traction means, to take a bistable element successively towards an active position, position stable and blocked therefore allowing relaxing of the effort, then subsequently by the same manoeuvre as the preceding one, to disengage the element from this active position and control the progressive and controlled return of the element towards its inactive, stable starting position.

To that end, the invention relates to a device for remote-control by a single manoeuvre of at least one element such as a gripping element formed by articulated elements and adapted to close, converging upon the object to be gripped, the device ensuring a blocking of said elements in their active position, while allowing in this stable position a relaxing of the control manoeuvre, characterized in that it comprises:

a) a rotating element such as a primary pulley connected to a control means such as a cable wound and driven in rotation by the traction of said cable;
  b) a spring returning the pulley towards its initial position against the action of said cable;
  c) a secondary pulley connected to the end of an output cable, this latter terminating by its opposite end at the gripping elements;
  d) disengageable mechanical drive means transmitting the torque from the primary pulley towards the secondary pulley;
  e) means for blocking the secondary pulley, adapted to immobilize the secondary pulley for a predetermined value of said torque, corresponding to the active position.

According to a more particular form of embodiment, the primary pulley and the secondary pulley are arranged on a common shaft, and the disengageable drive means are constituted by two discs, viz. a driving disc fast in rotation with the primary pulley and a driven disc fast in rotation with the secondary pulley, the discs presenting on each of their opposite faces surface unevenness, adapted to ensure, upon contact of the two discs by their opposite faces, the drive of the disc driven by the driving disc.

More especially, within the framework of this embodiment, the opposite faces of the respectively driving and driven discs comprise asymmetrical teeth forming on one side of the tooth an inclined plane forming a cam, the teeth being regularly distributed over the periphery of each disc and being separated by hollow housings of complementary profile, allowing the engagement of the teeth fast with a disc in the housings of the opposite disc when the two discs are in the engaged position, the slope of said inclined planes being such that, for values of the torque applied to the driving disc less than a determined threshold value, the two discs, driving and driven, are fast in rotation, while, for a torque attaining this critical value, further to the resistance opposed by the gripping elements having arrived in position of abutment on the object, said resistance transmitted by the output cable and the secondary pulley, the teeth of the driving disc slide freely on the teeth, then immobilized, of the driven disc, by their opposite inclined planes, which, by cam effect, provokes the axial translation of the secondary disc thus pushed by the driving disc towards the disengaged position of the drive means.

In particular, the inclined planes of the teeth of the driving disc slope downwards in the direction of rotation of the driving disc in action for the gripping manoeuvre, while the inclined planes of the teeth of the driven disc slope upwards in the direction of this same rotation, all these inclined planes being of the same angle and being opposite and thus being in contact from one disc to the other, when the drive means are in the engaged position.

According to another characteristic, the teeth of the discs comprise at their apex a flat portion, defining for each tooth a planar face parallel to the mean plane of the discs and forming a foundation for rest of the flat portion of the tooth located opposite, when the drive means are in disengaged position.

Advantageously, the side of each tooth opposite the inclined plane is orthogonal with respect to the plane of the disc, each tooth thus having a rectangular trapezoidal section.

According to an advantageous embodiment of the invention, the secondary pulley and the driven disc form a one-piece assembly, the driven disc being formed by a cheek of the secondary pulley, oriented towards the driving disc, being thereopposite.

Likewise, the secondary pulley is associated with a return spring, such as a helicoidal spring surrounding said shaft and adapted to return the secondary pulley towards its position of abutment, by its cheek forming driven disc, on the driving disc.

The element for blocking the secondary pulley in the position of gripping of the gripping elements is in particular constituted by a ring facing the cheek of the secondary pulley opposite the cheek in contact with the driving disc. This locking ring, on the one hand, and the opposite cheek of the secondary pulley, on the other hand, comprise surfaces provided with unevenness cooperating together from one face to the other in order to ensure blockage of the pulley in position, when the latter is brought into contact with said ring by the axial thrust undergone from the driving disc during the phase of slide of the teeth of the driving disc rising and pushing the inclined planes of the driven disc fast with the secondary pulley; to that end, the locking ring is provided at a distance from the secondary pulley equal to or less than the height of the trapezium formed by each of the teeth of the driving disc, said height corresponding to the axial stroke of translation of the secondary pulley, under the thrust of the teeth forming cams of the driving disc, in order to come into contact with the locking ring.

The flat portions located at the apex of the teeth comprise, at least on the driven disc, and preferably in the vicinity of the right angle starting the orthogonal side of the tooth, a projecting boss forming stop for the opposite tooth fast with the driving disc, this stop making it possible to mark and make aware for the user the mutual positioning of the teeth in disengaged position of the drive and of blocking of the secondary pulley, this boss being, in addition, of such section and height as to allow the tooth fast with the driving disc to surmount it and pass beyond, dropping in the following housing of the driven disc, when the torque exerted by the driving disc has gone beyond said critical threshold.

The mechanical transmission between the primary pulley and the driving disc is effected via a hub mounted for unidirectional rotation on the shaft of the device via a ratchet wheel and pawl assembly of the so-called "free wheel" type, adapted to ensure drive in rotation of the driving disc by the primary pulley in the direction of rotation corresponding to the transmission of the effort of traction on the traction cable, the driving disc being disconnected from the primary pulley upon rearward return of the latter under the action of its return spring, ensuring rewinding of the primary cable on its receiving primary pulley, without action on the driving disc.

The ring locking the secondary pulley is also mounted for unidirectional rotation by a ratchet and pawl assembly of the "free wheel" type, allowing a rotation of the ring with the secondary pulley in the direction of winding of the output cable and opposing any reverse rotation with rearward return of the output cable and gripping elements. The latter are thus blocked in this set position of equilibrium, by abutment of the secondary pulley on the locking ring, until a fresh traction from the cable generates the excess rotation of the driving disc, beyond this position of equilibrium, and provokes the return of the teeth of the driving disc in the next housings of the driven disc. This fresh mutual engagement of the teeth on the two discs provoking the axial translation of the secondary pulley under the thrust of its return spring, said pulley resuming its initial position of engagement on the driving disc via its cheek forming driven disc, and at the same time the secondary pulley then escapes from its engagement on the locking ring.

The groove for winding the traction cable on the primary pulley is provided with a radius greater than that of the groove for winding the output cable on the secondary pulley, thus allowing a demultiplication between the stroke of the traction cable and that of the output cable, the assembly constituting a pulley block allowing a greater precision in the control of the manoeuvre and a better yield of the effort in the gripping manoeuvre.

It may also be provided that the primary pulley comprises a recessed part on its periphery over a substantially semi-circular segment of crown, the non-recessed sector bearing on its periphery, substantially in a semi-circle, the groove for winding the traction cable, the central crown of the pulley comprising a plurality of regularly distributed housings for receiving the engagement of the end of a return spring working in torsion, the suitable choice of the housing possibly making it possible to calibrate the return force exerted on the primary pulley.

According to the preferred embodiment hereinabove, (the device) is inserted and contained in a housing provided with openings respectively for the traction and output cables, and the housing is mounted fast with a plate forming structure of an artificial hand, the output cable terminating, in manner known per se, in a single beam for distributing the traction on the terminal cables each serving a finger, each finger being able to be brought into bent position against the action of a spring, the traction cable being connected upstream to a manoeuvring harness worn by the user.

Other characteristics and advantages of the invention will further appear from the following description, given by way of non-limiting example with reference to the accompanying drawings, in which.

Figure 7A:
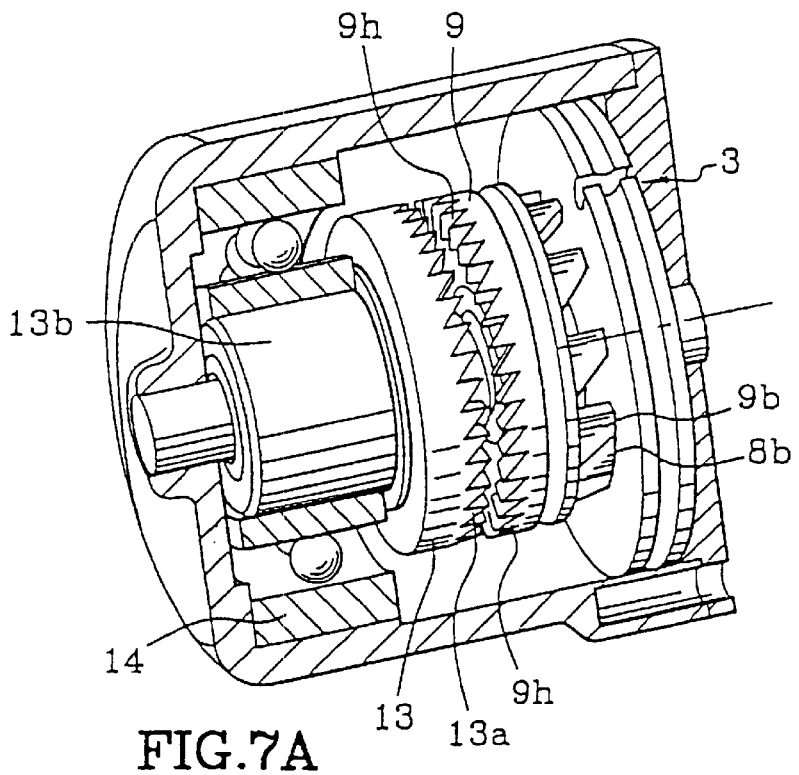
Figure 7B:
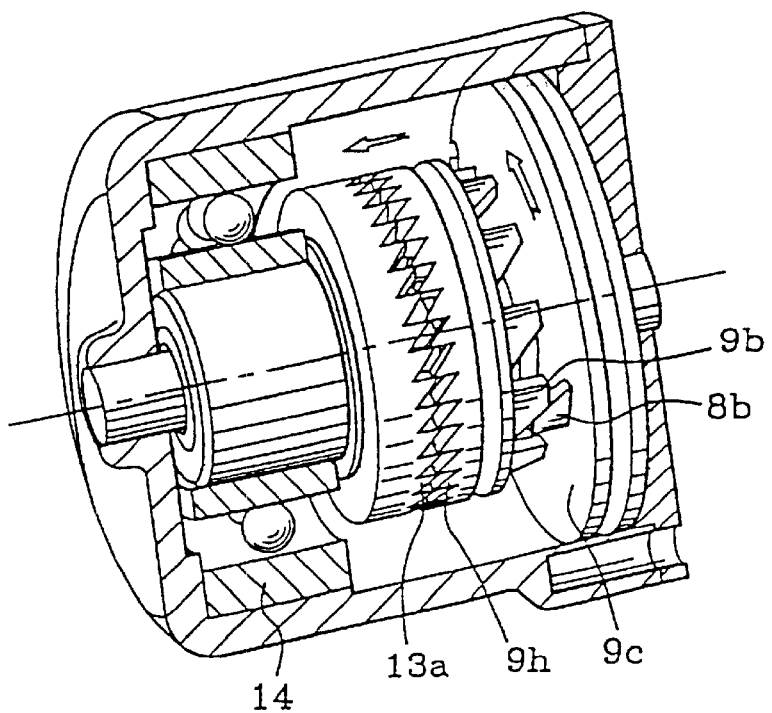
Figure 7C:
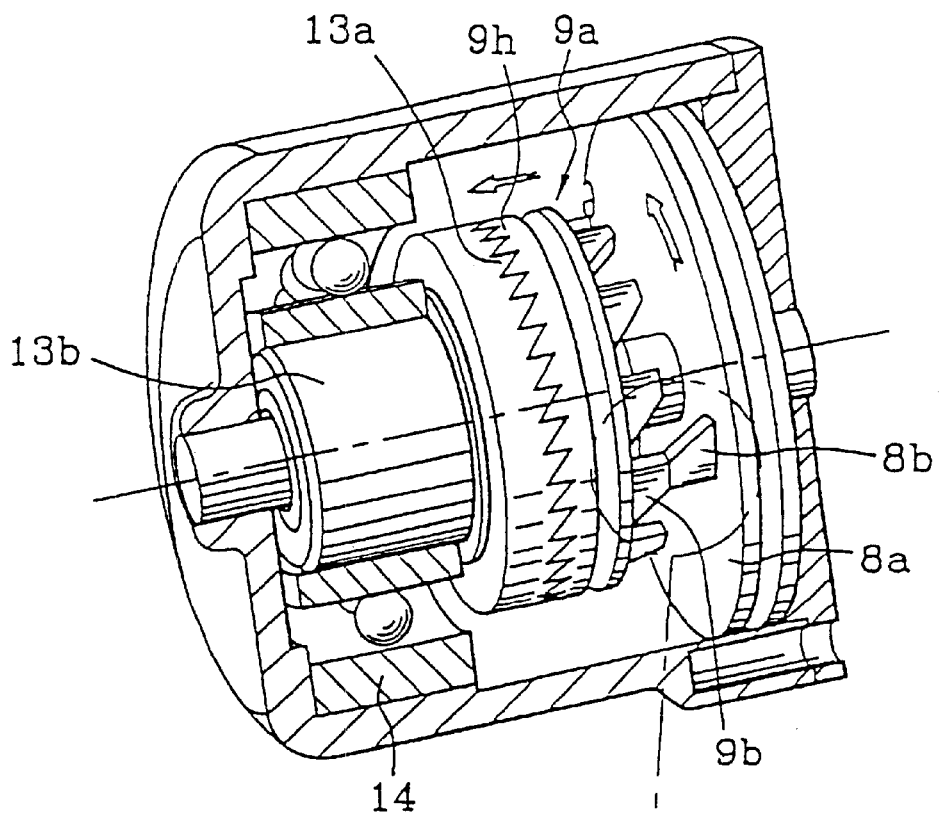
Figure 7C:
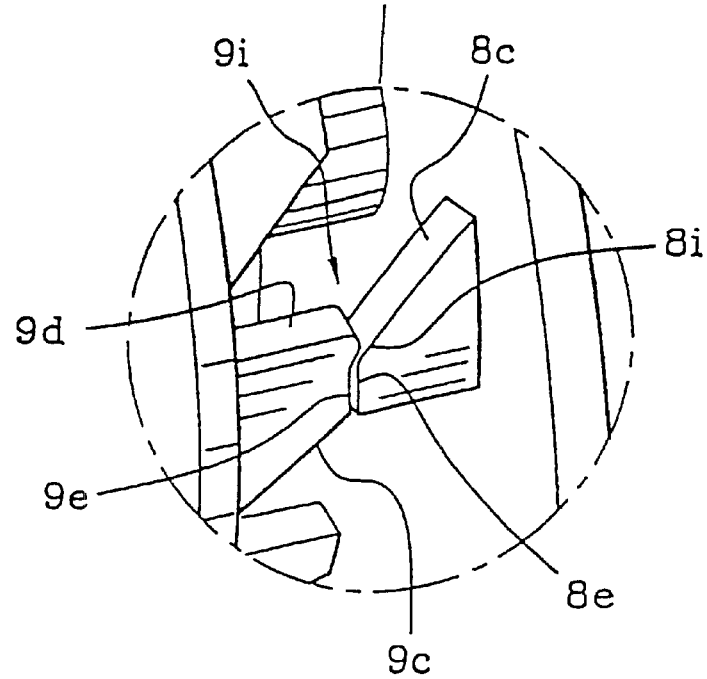

FIGS. 7A, 7B and 7C are exploded views in perspective showing the elements composing the device of the invention respectively in initial position, the transmission towards the output cable being engaged (7A); in the intermediate position, the secondary pulley being in the process of translation towards its disconnected position (7B); and finally, in the disconnected position of the secondary pulley, then in locked position by engagement on the locking ring (7C).

Figure 8:
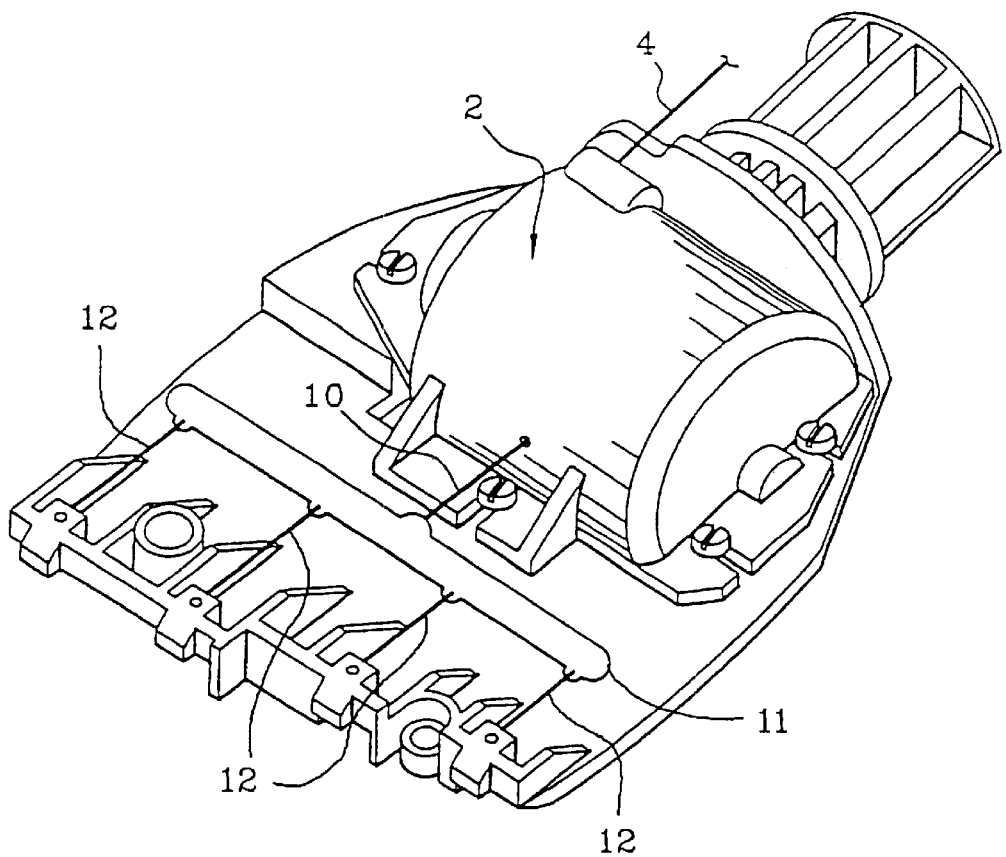

FIG. 8 is a view in elevation of the device of the invention positioned on a receiving plate forming the basic structure of an artificial hand.

Figure 1:
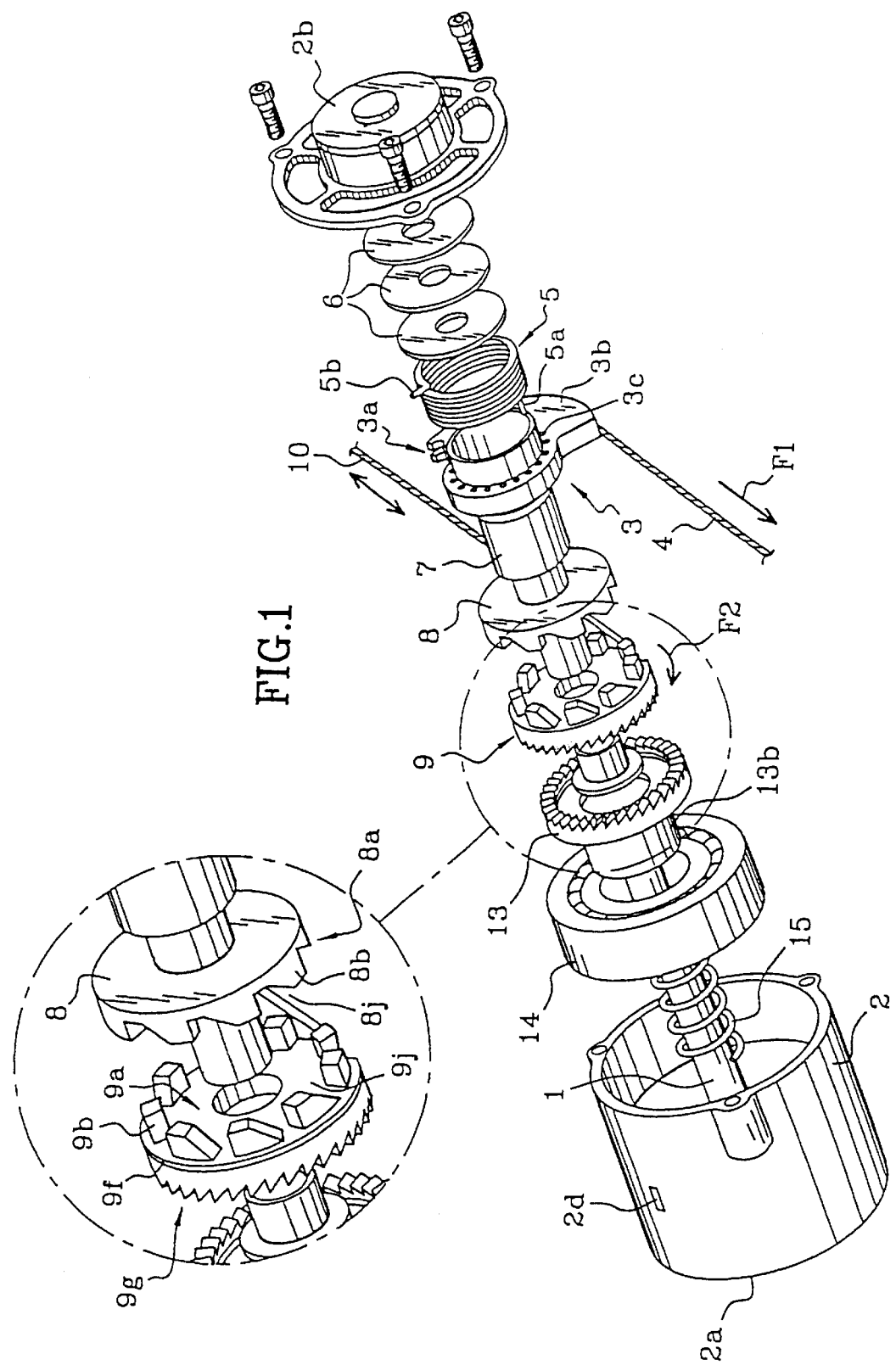
FIG. 1 is an exploded view of the various elements coming within the mechanism according to the invention.
Figure 2:
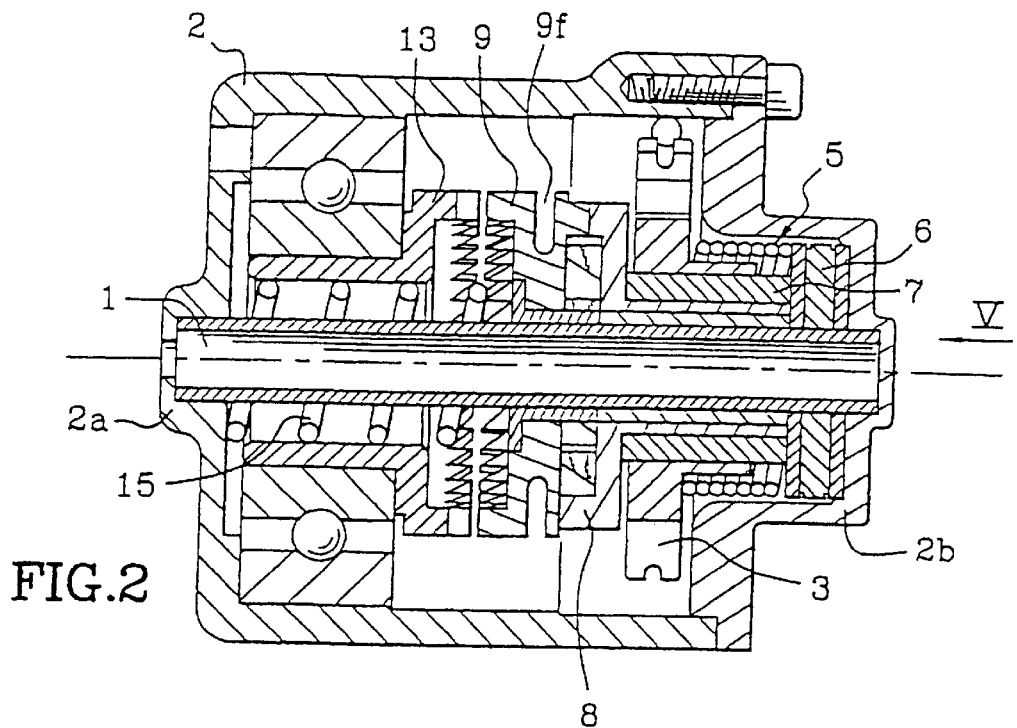
FIG. 2 is a view in section of the device, along line II—II of FIG. 5, in a position of the driving disc engaged on the driven disc.

According to all the Figures, particularly FIGS. 1 and 2, it is seen that the movement transmission device according to the invention is composed of a fixed shaft 1 enclosed in a housing 2 constituted by a blind cylindrical body obturated at one end by a bottom 2a and at the opposite end by the circular dish 2b bolted on the cylindrical body 2. On this shaft 1 is mounted a pulley, so-called primary pulley 3, provided with a groove 3a for receiving the cable 4 forming traction cable and moved by the user from a scapular or dorsal harness (not shown) in manner known per se.

Figure 6:
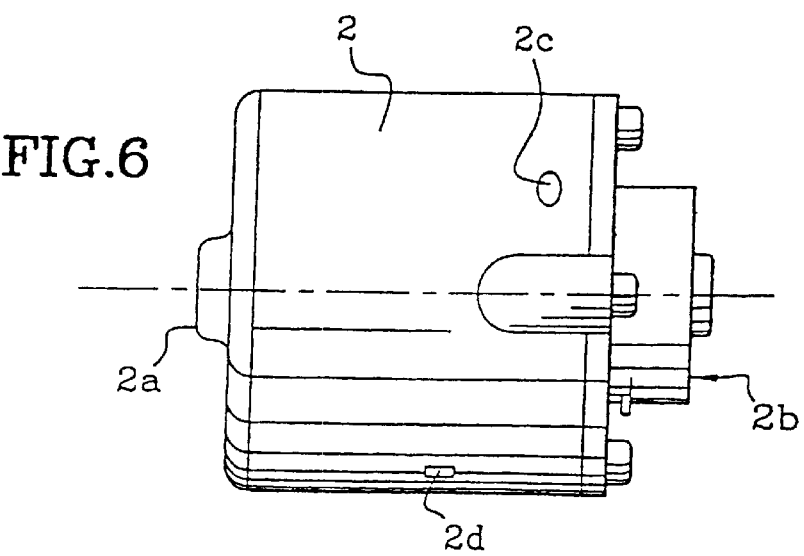
FIG. 6 is a view in side elevation of the device contained in its housing.

The housing comprises output slots or orifices, respectively 2c for the admission of the traction cable 4, and 2d for the exit of the output cable 10 (FIG. 6).

Advantageously, the pulley 3 is largely recessed along a peripheral crown segment as shown in FIG. 1; the remaining central part 3b is provided with housings 3c distributed over this crown and adapted to receive the bearing end 5a of the helicoidal spring 5 working in torsion. The opposite end 5b of said spring is immobilized on a fixed bearing (not shown) provided on the inner face of the dish 2b. This helicoidal spring constitutes a return spring returning the primary pulley 3 and the cable 4 towards the rest position, the cable in that case not undergoing any effort of traction from the user.

That part of the shaft 1 close to the dish 2b comprises means allowing the free rotation of the primary pulley in the direction of traction and in the direction of its return under the action of the spring; these means are in particular constituted by needle bearings 6 (FIG. 2).

The primary pulley is engaged on the hub 7 itself mounted to rotate on the sleeve 8a fast with the driving disc 8 journalled on the shaft 1; the hub 7 constitutes a unidirectional drive interface between the pulley 3 and the driving disc 8 and it comprises to that end an assembly of known type constituted by a pawl returned against a ratchet wheel of the "free wheel" type, such that, in the direction of drive of the pulley 3 actuated by the traction cable (arrow F1, FIG. 1), the manoeuvre is transmitted to the driving disc 8. While in the opposite direction, the pulley being returned by the spring 5, the disc 8 remains in its position, no longer being kinetically fast with the pulley.

The driving disc 8 bears on its face 8a, opposite the primary pulley 3, parts in relief cooperating with parts in relief fast with the face 9a of the driven disc, here formed by the cheek of the secondary pulley 9, cheek disposed opposite the driving disc 8. In the embodiment shown and described, these parts in relief are constituted by teeth 8b (on the driving disc) and 9b (on the cheek 9a of the secondary pulley 9) respectively, cf. FIGS. 7A, 7B and 7C. The teeth are distributed on the peripheral circumference of each of the faces 8a and 9a, the teeth being oriented point by point from one face 8a to the other 9a. As developed in FIG. 7C, each tooth follows the shape of a rectangular trapezoidal section of which the large base is constituted by the line of contact of the tooth with its support disc; one side is an inclined plane 8c, 8d, and the opposite side 8d, 8d is orthogonal to the plane of the support disc, the small base of the trapezium located at the apex of the tooth forms a flat portion 8e, 9e.

These teeth are of identical shapes on the driving disc 8 and the cheek 9a, but the slopes of the inclined planes 8c, 9c are reversed between the driving disc 8 and the cheek 9a of the secondary pulley, acting as driven disc. The slope of the inclined plane 8c descends in the direction of drive of the driving disc from the primary pulley 3; the slope of the inclined plane 9c ascends in this same direction (arrow F2, FIG. 1).

As the teeth are disposed on their support discs, being spaced apart by an interval or pitch corresponding to the large base of each tooth, and taking into account the reversal of the slopes, the interval or gap 8*j*, 9*j* (FIG. 1) between two teeth of a disc is complementary of the tooth located opposite on the opposite disc and facing it. In this way, the teeth of the respectively driving and driven discs may interpenetrate, each tooth being placed in the receiver housing constituted by the interval between two teeth of the opposite disc. The assembly thus forming a dog-clutch type drive.

On its peripheral circumference, the secondary pulley 9 comprises a groove 9*f* receiving an output cable 10; this latter, as related and shown in greater detail in the French Patents cited hereinabove, terminates in a beam 11 for distribution of the traction effort retransmitted to the terminal cables 12 each controlling the manoeuvre of an individual finger (FIG. 8).

The cheek 9*g* of the secondary pulley 9, opposite the cheek 9*a*(FIG. 1) faces a ring 13 ensuring an intermittent blocking of the pulley 9; for the purposes of the blocking manoeuvre, the opposite faces of the ring 13 and of the cheek 9*a* comprise parts in relief or uneven surfaces, cooperating from one face to the other to ensure this effect of blocking when the two faces are brought into contact, under the conditions described hereinafter. In the example described and shown, this surface unevenness is advantageously constituted by teeth 13*a* and 9*h* disposed as a crown and tête-à-tête from one face with respect to the other, the teeth thus being adapted to come into position of mutual engagement (FIGS. 7A, 7B and 7C).

The ring 13 is itself fast with a sleeve 13*b* extending along the shaft 1 in the opposite direction to the face of the ring bearing the teeth 13*a* and this sleeve is blocked inside a roller bearing 14, itself mounted inside the walls of the housing 2 and immobilized by its outer ring; this bearing 14 comprises a pawl assembly bearing on a ratchet wheel, of the "free wheel" type with unidirectional rotation. The ring 13 is thus free to rotate in the direction of drive of the secondary pulley 9 (arrow F2, FIG. 1), itself driven from the driving disc 8, but the opposite direction remains prohibited for the ring; in this way, the locking ring 13 is adapted, when it is in position of engagement by its toothed face 13*a* on the toothed face 9*g* of the secondary pulley, to accompany the rotation of the secondary pulley freely; while the rearward return of the ring from this movement is not allowed by the unidirectional bearing or "free wheel" 14; with the result that the pulley 9 having effected an angular movement, with traction transmitted to the output cable, and in that case being in engagement contact with the ring 13, is indeed blocked in this position without rearward return, this acquired position of equilibrium being maintained as long as the pulley 9 and ring 13 remain in contact, their disengagement like their engagement thus being effected as described hereinafter.

A spring 15 of the helicoidal type, bearing on one side on the bottom 2*a* of the housing 2 and on the other side on the cheek 9*g* of the secondary pulley 9, tends to elastically push the secondary pulley 9, along the shaft 1, towards the position of abutmnt of the secondary pulley 9 on the driving disc 8.

Functioning of the assembly thus described may be set forth as follows:

In the initial rest position, no effort of traction yet being exerted on the traction cable 4, the elements described are in the position shown in FIGS. 2 and 7A; the primary pulley is in its rest position in abutment on its seat, the spring 5 being under weak tension; the driving disc 8 is in position of engagement by its trapezoidal teeth in the housings constituted by the intervals between the teeth of the opposite cheek belonging to the secondary pulley 9. This pulley is itself, under the action of the spring 15, applied against the driving disc in the position of engagement of the teeth, and maintained distant from its position of contact and engagement with the locking ring 13, in that case inactive.

At the beginning of manoeuvre with a view to an operation of gripping of any object, the user exerts from a harness of known type a traction on the traction cable 4, which drives the primary pulley 3 in rotation against the action of the spring 5; this movement is communicated by the free wheel hub 7 to the driving disc 8, in that case in dog-clutch position on the secondary pulley 9. The latter is thus in turn driven in rotation, which makes it possible to transmit the initial force of traction exerted on the cable 4 up to the output cable 10. The latter may thus exert a linear traction on the distribution beam assembly from which the traction is reverberated on the terminal cables, provoking the successive bending of the fingers as set forth in the French Patents mentioned hereinbefore.

Such bending of the fingers converging upon the object to be gripped terminates in their position of abutment on the walls of this object, position in which the fingers being in abutment on this object resist the continuation of the movement; this force of reaction is then transmitted by the terminal cables and the output cable 4 up to the secondary pulley 9, in that case prevented from continuing its movement and resisting the torque coming from the driving disc.

Figure 3:
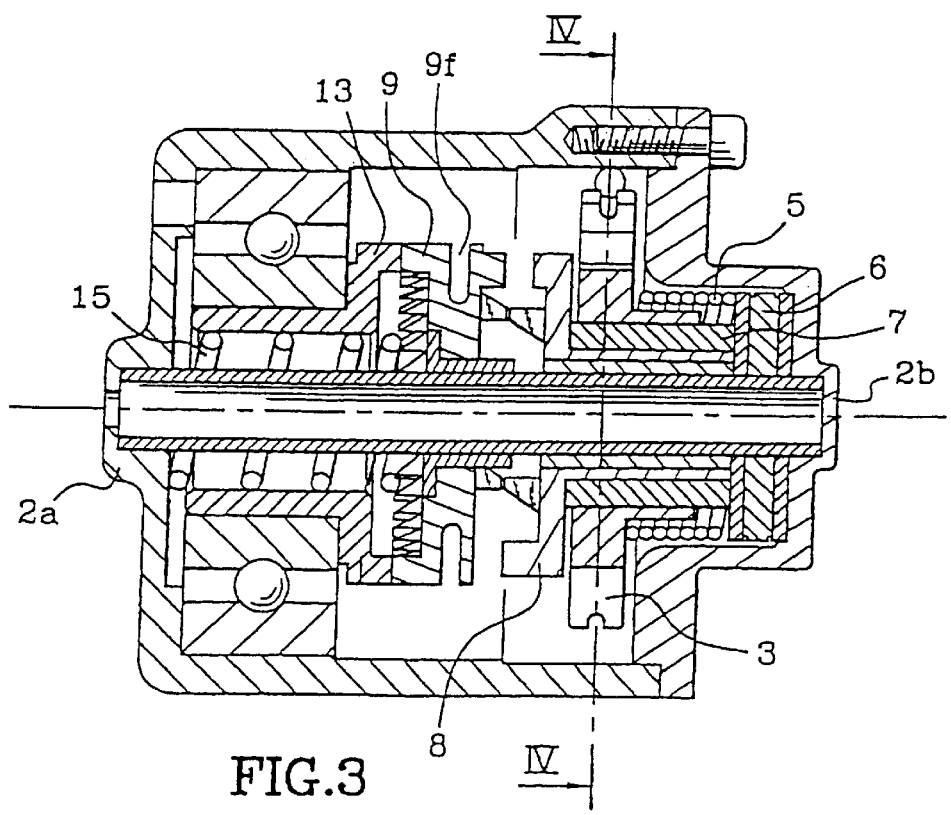
FIG. 3 shows the same view as FIG. 2, in the disconnected position of said transmission.
Figure 4:
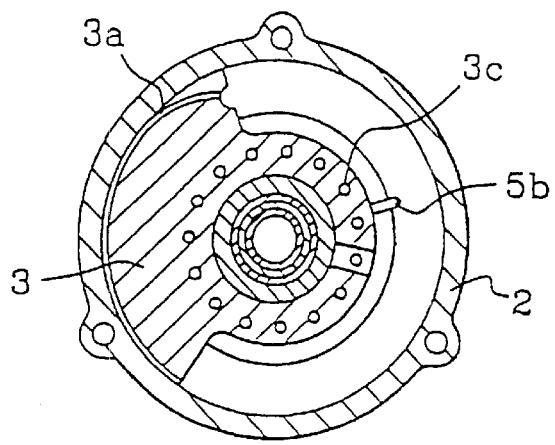
FIG. 4 is a view in section of the device of FIGS. 2 and 3, along line IV—IV of FIG. 2.
Figure 5:
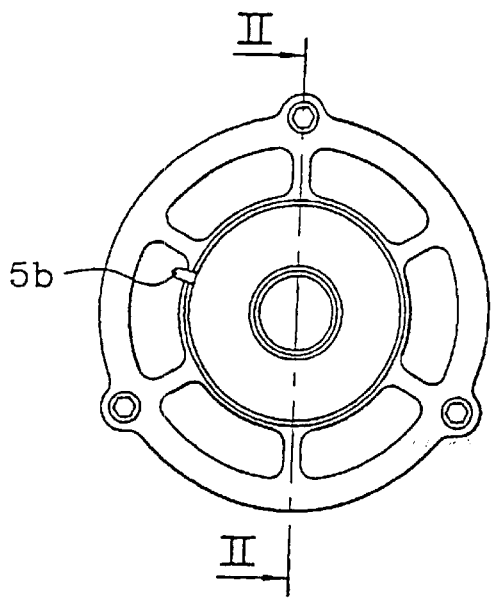
FIG. 5 is a view in front elevation of the device seen in the direction of arrow V of FIG. 2.

The user continuing his/her effort of traction on the cable 4, maintains the torque on the driving disc 8 in abutment on the face 9*a* of the pulley 9, the latter remaining, however, in position of immobilization. In this combined operation of rotary action on the driving disc and of corresponding reaction of the opposite cheek of the secondary pulley, the inclined planes of the teeth of the driving disc 8 and of the cheek 9*a* of the secondary pulley respectively, perform the role of cam and, by mutual slide, slope against slope, of one tooth on the opposite tooth, allow a limited continuation of the rotation of the driving disc, accompanied by an axial thrust exerted by the driving disc 8 against the secondary pulley 9, which is pushed in the direction of the locking ring 13, against the action of the spring 15, until the flat portions 8*e* at the apex of the teeth of the driving disc rest on the opposite flat portions 9*e* of the teeth of the cheek 9*a* of the secondary wheel. This manoeuvre of slide of the teeth on one another is represented in FIGS. 7A and 7B in which, in order to render the drawings clear, only one tooth 8*b* fast with the driving disc has been shown. The position of the teeth resting against one another by their respective flat portions is illustrated in FIG. 7C. To render the drawings clear, these FIGS. 7A, 7B and 7C have shown only one tooth 8*a* fast with the driving disc 8. As for FIG. 3, it only shows two teeth of the driving disc in opposition on two teeth of the driven disc; it will be noted that the teeth seen in FIGS. 2 and 3 belonging to the concave or rear part of the crown of the teeth, since these Figures are views in section, therefore in which the teeth located on the reader's side, above the Figure, are not visible.

In this position (flat portion against flat portion) of said teeth, the secondary pulley 9 is displaced axially by a distance corresponding to the height of the trapezoidal teeth, i.e. the secondary pulley has covered exactly the distance which separated it from the locking ring 13. The respective toothings of the locking ring and of the opposite cheek 9*g* of the secondary pulley are then brought into position of engagement and the ring, being mounted in unidirectional rotation, opposes any rearward return of the pulley then blocked in position.

The limited rotation of the driving disc 8 may continue over some degrees, always under the voluntary control of the user, the teeth sliding on one another by their flat portions in contact, until the tooth of the driving disc bears on a boss 9i forming stop arranged on the flat portion 9e of the opposite tooth 9h, fast with the cheek 9a of the secondary pulley (FIG. 7C) near the right angle formed between the flat portion 9e and the orthogonal side 9d of the tooth. This stop marks for the user and by the increase in the resistance encountered, the stop of the manoeuvre of traction, corresponding to a position of equilibrium of the assembly; the stop therefore facilitates for the user the obtaining of this position of equilibrium by absorbing the inertia of the pieces in movement until then, and making him aware of the position.

In the position of equilibrium thus attained, the manoeuvre of gripping by the fingers is blocked and the object seized is held by the artificial hand; the locking ring in effect prevents a rearward rotation of the secondary pulley and consequently a relaxing on the output cable and therefore on the terminal cables serving each of the fingers. The position therefore being blocked, the user can relax his effort of traction and give all his attention and motricity to manoeuvring the displacement or use of the object seized.

Upon relaxing of the effort of traction, the spring 5 returns the primary pulley 2 into its starting position, the end of the cable 5 close to the pulley being rewound on the latter. However, this rearward return of the pulley 3 is effected without corresponding drive of the driving disc remaining blocked by contact, teeth against teeth and flat portions against flat portions, on the opposite cheek of the secondary pulley, itself pushed against the driving disc by its return spring 15. As set forth previously, the free wheel hub 7 allows this rearward rotation of the primary pulley, without affecting the driving disc.

Then from this manoeuvre and when the object must be released in order to be deposited, the user exerts a traction on the cable 4, generating at the level of the driving disc a torque of a sufficient value to allow each tooth 8b of the driving disc to jump over the boss 9i previously described and constituting stop for the position of equilibrium, the object in that case being in position of gripping. To that end, the obtuse angle 8i of the tooth of the driving disc coming opposite is provided with a slightly rounded apex, facilitating passage (FIG. 7C).

The subsequent rotation of the driving disc takes the teeth of the disc to the level of the housings provided on the opposite cheek of the secondary pulley, housings constituted by the intervals between the teeth of this cheek, and these housings being, as described previously, of shape complementary of the teeth located opposite, these teeth are adapted to be positioned in these intervals. The spring 15 pushes the cheek 9g of the secondary pulley against the driving disc, whose teeth fit in the receiving intervals between the teeth of the cheek 9g. The teeth are thus in their position of engagement or of mutual dog-clutching, such as at the beginning of the manoeuvre, after angular displacement by some degrees, corresponding to the length of the large base of the trapezoidal tooth. This manoeuvre of mutual re-engagement of the teeth, towards the dog-clutching position, is then obtained by axial translation of the secondary pulley, under the thrust of its return spring 15, as soon as the orthogonal side of the driving tooth is positioned beyond the orthogonal side of the teeth located opposite, eliminating the anterior flat portion against flat portion bearing.

The return of the secondary pulley 9 towards the driving disc 8 disengages the latter from its position of engagement on the locking ring; however, the object remains held in the hand since the voluntary traction from the cable 4 is transmitted by the system up to the terminal cables; the user may then, as desired, maintain or relax his effort in order to loosen the grasp and abandon the object in the desired position.

The system possibly enables the user, having changed his mind, to resume, by a continued traction on the cable 4, the position of blocking of the artificial hand on the object, under the conditions set forth hereinabove.

The radius of the groove 3A for winding the traction cable 4 on the pulley 3 is larger than the radius of the groove of the secondary pulley 9, receiving the output cable 10, with the result that the transmission of the force of traction is effected with an effect of demultiplication, allowing a better precision in the gestural or digital control and a better yield of the effort exerted by the user.

The artificial hand using the means of the invention also comprises, apart from the four fingers (fore-finger, middle finger, ring finger and little finger) controlled by the terminal cables, a mobile thumb with autonomous manoeuvre and functioning for example as set forth in the Certificat of Addition 74 23597 to French Patent 73 25719 mentioned above.

The invention thus allows the control of the manoeuvre of an artificial hand, in particular from a dorsal harness, with the possibility of effecting, after obtaining the position of gripping, the automatic locking the system in this position, allowing a relaxing of the effort of traction, releasing the activity of the subject, the object remaining held in the hand. Subsequently, unlocking may be obtained in autonomous manner by the same voluntary control of the single traction cable; the latter manoeuvred by harness therefore successively makes it possible, and without other intervention, to control locking in gripping position, then unlocking; the latter being effecteed while the user is at the same time recovering the voluntary control of the grip and may gradually loosen his grasp.

Such autonomy of the artificial hand reproducibly allowing the cycles of seizure in the hand, blocking of the seizure maintained with release of the effort, then resumption of the voluntary seizure manoeuvre, constitutes considerable progress over the prior known systems, knowing a blockage of the gripping position only by outside intervention.

The innovation forming the subject matter of the present description therefore brings a considerably improved functionality, allowing more rapid, more reliable and less difficult manoeuvres in the everyday operations of gripping applied to objects of various shapes and configurations.

It brings considerable comfort of use for the user, both from the practical and from the moral standpoint by reducing the feeling of abnormality thanks to aesthetics close to the natural hand. Using light materials, particularly synthetics, composities or light alloys, the artificial hand using the device of the invention remains at a non-handicapping weight. Various arrangements may be introduced, including in particular the motorization of the control of the traction cable with myoelectronic control. The traction cable with linear manoeuvre might be replaced by an angular control by rotary shaft directly meshing on the primary pulley 3.

The foregoing description has been given only by way of illustration and without limiting character, it being recalled that the transmisison, control, locking and demultiplication system of the invention may be applied to various manoeuvring, remote-control, particularly remote manipulation elements. The invention will be particularly applicable when one has available a single control means with unidirectional active manoeuvre, having to take a bistable element or system, successively in two positions, by one and the same control. A first control progressively brings the system, under control, towards an active position (for example gripping) in which it is locked and stabilized, no longer requiring a voluntary intervention. In a second step, the repetition of the same control, identical to the preceding one, unlocks the system while maintaining it in its active position and replaces it under voluntary control allowing its progressive return to the first position. The control, subject matter of the invention, is thus with double effect and therefore exploitable when, for constructive or ergonomic reasons in particular, there is available only one control with mono-directional action in order to obtain from a system its successive placing in two stable positions, in a cycle with two alternate phases and comprising:

the progressive rise towards an active position with final automatic locking in this acquired and set position;

the unlocking with hold in this active position allowing the progressive and controlled return towards the initial inactive position; each of the phases being controlled individually by the same manoeuvre of the same single and mono-directional control means, taking in charge the system in the state where it is found and bringing it under voluntary control in the alternative state.

What is claimed is:

1. Device for remote-control by a mono-directional action means of at least one gripping element comprising articulated elements and adapted to close, converging upon the object to be gripped, the device being adapted to ensure a blocking of said elements in their active position in contact with said object, allowing in this gripping position a relaxing of the control means, the device comprising:
   a) a rotating primary pulley connected to a control cable, and driven in rotation by the traction of said cable;
   b) a spring returning the pulley angularly towards its initial position against the action of said cable;
   c) a secondary pulley connected to the end of an output cable, this latter terminating by its opposite end at the gripping elements;
   d) disengageable mechanical drive means transmitting the torque from the primary pulley towards the secondary pulley; and
   e) means for blocking the secondary pulley, adapted to immobilize the latter for a predetermined value of said torque, corresponding to the gripping position.

2. Device according to claim 1, wherein the primary pulley and the secondary pulley are disposed on a common shaft, and the disengageable drive means are constituted by a driving disc fast in rotation with the primary pulley and a driven disc fast in rotation with the secondary pulley, the discs presenting on each of their opposite faces unevenness of surface adapted to ensure, upon contact of the two discs by their opposite faces, the drive of the driven disc by the driving disc.

3. Device according to claim 2, wherein the opposite faces of the respectively driving and driven discs comprises of asymmetrical teeth forming on one side of the tooth an inclined plane forming a cam, the teeth being distributed regularly over the periphery of each disc and being separated by recessed housings of complementary profile, allowing the engagement of the teeth fast with a disc in the housings of the opposite disc in the engaged position of the two discs, the slope of said inclined planes being such that, for values of the torque applied to the driving disc less than a determined threshold value, the two discs, driving and driven, are fast in rotation, while for a torque attaining this value, further to the resistance opposed by the gripping elements having arrived in position of abutment on the object, resistance transmitted by the output cable and the secondary pulley, the teeth of the driving disc sliding freely on the teeth, then immobilized, of the driven disc, by their opposite inclined planes, which, by cam effect, provokes the axial translation of the secondary disc thus pushed by the driving disc towards the disengaged position of the drive means.

4. Device according to claim 3, wherein the inclined planes of the teeth of the driving disc slope downwards in the direction of rotation of the driving disc in action for the gripping manoeuvre, while the inclined planes of the teeth of the driven disc slope upwardly in the direction of this same rotation, all these inclined planes being of the same angle and facing one other and thus being in contact from one disc to the other, in the engaged position of the drive means.

5. Device according to claim 3, wherein the teeth of the discs comprise at their apex a flat portion defining for each tooth a plane face parallel to the mean plane of the discs and forming a foundation for rest of the flat portion of the tooth located opposite, in the disengaged position of the drive means.

6. Device according to claim 3, wherein the side of each tooth opposite the inclined plane is orthogonal with respect to the plane of the disc, each tooth thus having a rectangular trapezoidal profile.

7. Device according to claim 1, wherein the secondary pulley and the driven disc form a one-piece assembly, the driven disc being formed by a cheek of the secondary pulley oriented towards the driving disc, facing it.

8. Device according to claim 7, wherein the secondary pulley is associated with a helicoidal spring surrounding said shaft and adapted to return the secondary pulley towards its position of abutment, by its cheek forming driven disc, on the driving disc.

9. Device according to claim 2, wherein the element for blocking the secondary pulley in the gripping position of the gripping elements is constituted by a ring facing a cheek of the secondary pulley, this locking ring, on the one hand, and the opposite cheek of the secondary pulley, on the other hand, comprising surfaces provided with unevenness cooperating together from one face to the other to ensure locking in position of the pulley when it is brought into contact with said ring by the axial thrust undergone from the driving disc during the phase of slide of the teeth of the driving disc rising and pushing the inclined planes of the driven disc fast with the secondary pulley, and, to that end, the locking ring is provided at a distance from the secondary pulley equal to or less than the height of the trapezium formed by each of the teeth of the driving disc, height corresponding to the axial stroke of translation of the secondary pulley, under the thrust of the teeth forming cams of the driving disc, in order to come into contact with the locking ring.

10. Device according to claim 5, wherein the flat portions located at the apex of the teeth of the driven disc, and near the right angle starting the orthogonal side of the tooth, a projecting boss forming a stop for the opposite tooth fast with the driving disc, the stop making it possible to mark and make aware for the user the mutual positioning of the teeth in disengaged position of the drive and of blocking of the secondary pulley, the boss further being of a profile and of a height allowing the tooth fast with the driving disc to surmount it and pass beyond, dropping in the following housing of the driven disc, when the torque exerted by the driving disc has exceeded said threshold, and to that end, the obtuse angle formed on each tooth of the driving disc is rounded at its apex, in order to facilitate this passage.

11. Device according to claim 1, wherein the mechanical connection between the primary pulley and the driving disc is effected via a hub mounted for unidirectional rotation on the shaft of the device via a ratchet wheel and pawl assembly of a free wheel type, adapted to ensure drive in rotation of the driving disc by the primary pulley in the direction of rotation corresponding to the transmission of the effort of traction on the traction cable, the driving disc being disconnected from the primary pulley upon rearward return of the latter under the action of its return spring, ensuring the rewinding of the primary cable on its receiving primary pulley, without action on the driving disc.

12. Device according to claim 10, wherein the locking ring of the secondary pulley is mounted for unidirectional rotation by a ratchet and pawl assembly of a free wheel type, allowing a rotation of the ring with the secondary pulley in the direction of winding of the output cable and opposing any reverse rotation with rearward return of the output cable and of the gripping elements, thus blocked in this position of equilibrium acquired and fixed by abutment of the secondary pulley on the locking ring, until the excess rotation of the driving disc, beyond this position of equilibrium, provokes the return of the teeth of the driving disc in the next housing of the driven disc, the fresh mutual engagement of the teeth on the two discs being provoked by the axial translation of the secondary pulley under the thrust of its return spring, said pulley resuming its initial position of engagement on the driving disc via its cheek forming driven disc, and the secondary pulley then escaping from its engagement on the locking ring.

13. Device according to claim 1, wherein the groove for winding the traction cable on the primary pulley is provided with a radius greater than that of the groove for winding the output cable on the secondary pulley, thus allowing a demultiplication between the stroke of the traction cable and that of the output cable, the assembly constituting a pulley block allowing a greater precision in the control of the maneuver and a better yield of the effort in the gripping maneuver.

14. Device according to claim 1, wherein the primary pulley comprises a part recessed on its periphery over a substantially semicircular crown segment, the non-recessed sector bearing on its substantially semicircular periphery the groove for winding of the traction cable.

15. Device according to claim 1, wherein the device is inserted and contained in a housing provided with openings respectively for the traction cable and output cable, and the housing is mounted fast with a plate forming structure of an artificial hand, the output cable terminating in a single beam for distribution of the traction on the terminal cables each serving a finger, brought into bent position against the action of a spring, the traction cable being connected upstream to a maneuvering harness worn by the user.

\* \* \* \* \*